US005704160A

United States Patent [19]
Bergquist et al.

[11] Patent Number: 5,704,160
[45] Date of Patent: Jan. 6, 1998

[54] PRODUCTION METHOD FOR HIGH-OIL CORN GRAIN

[75] Inventors: Richard Robert Bergquist, El Paso; Douglas Stuart Nubel, Bloomington, both of Ill.; Donald L. Thompson, Raleigh, N.C.

[73] Assignees: E. I. Du Pont de Nemours and Company; DuPont TopCross International, Inc., both of Wilmington, Del.

[21] Appl. No.: 615,839

[22] Filed: Nov. 16, 1990

[51] Int. Cl.$^6$ .............................. A01H 1/00; A01H 5/00
[52] U.S. Cl. ............................ 47/58; 800/200; 800/250; 800/DIG. 56
[58] Field of Search ............ 47/58, 58.03, 58.04; 800/200, 250, 205, DIG. 56; 435/172.2

[56] References Cited

U.S. PATENT DOCUMENTS 5,004,864  4/1991  Robertson et al. ................... 800/235

OTHER PUBLICATIONS

Poehlman (1987) *Breeding Field Crops*, AVI Publishing Company, Inc. Westport Connecticut. pp. 76–79, 246, 457–460, 469–471, 473, 500 snf 502.

Alexander et al. (1977) *Corn and Corn Improvement: Breeding Special Industrial and Nutritional Types*. ASA publication #18, second edition. p. 363.

D.E.Alexander and R.J. Lambert,Relationship of Kernel Oil Content to Yield in Maize, 1968, Crop Science, 8, 272–274.

Misevic, D. Population Cross Diailele among High Oil Populations of Maize, 1989, Crop Science, 29, 613–617.

D.E.Alexander, High Oil Corn: Breeding and Nutritional Properties, 1988, 43rd Annual Corn and Sorghum Research Conference, pp. 97–105.

Fundamentals of Plant Cultivation, 5th Revised and Expanded Edition, Walter De Bruyter, Berline, New York 1985.

Ruslov. (1974) Institut po tsareuitsata, vol. 7(5) pp. 353–360 (Pl.Breeding Abstract 1973+).

Allard. (1960) *Principles of Pl. Breeding* p. 468.

*Primary Examiner*—Gary Benzion
*Attorney, Agent, or Firm*—Bruce W. Morrissey

[57] ABSTRACT

A novel method of producing corn grain with a high oil content has been developed. Through pollination of male-sterile hybrid corn plants by nonisogenic corn plants possessing the trait of high-oil, grain is obtained possessing an oil content much higher than would be expected for self- or cross-pollination. This method can be practiced by farmers using currently accepted farming practices to directly obtain high yields of high-oil corn grain for animal feed and other products.

14 Claims, No Drawings

1

PRODUCTION METHOD FOR HIGH-OIL CORN GRAIN

FIELD OF THE INVENTION

This invention teaches a novel method of corn grain production wherein female corn plants, obtained from a high-yielding variety, are grown with and pollinated by nonisogenic corn plants possessing genes which control the expression of high amounts of oil in the grain. Following this pollination, grain harvested from the female plants will contain a significantly greater amount of oil than what would be obtained following self- or cross-pollination of male-fertile or male-sterile versions of the female hybrid.

BACKGROUND OF THE INVENTION

Corn is a major crop used as a human food source, an animal feed, and as a source of carbohydrate, oil, protein, and fiber. It is principally used as an energy source in animal feeds, or as a raw material for the recovery of starch, protein feed fractions, fiber, flaking grits, flour, and oil. The number of products produced from corn or components extracted from corn are numerous, and include, among others, paper sizings, high fructose corn syrup, adhesives, food thickeners, industrial and medical absorbants, and ethanol (from starch); animal feed and feed components (from whole grain, corn silage, corn gluten feed and meal), and corn oil which is extracted from the germ.

Virtually all commercial corn produced in the United States, Canada, and Europe, and much of the corn produced in South America, is produced from hybrid seed. The production of corn hybrids requires the development of elite corn inbred lines that demonstrate good general and specific combining ability in order that they produce agronomically superior hybrids. Among the traits that plant breeders select for in producing hybrids are high yield potential, good stalk strength, resistance to specific diseases, reasonable drought tolerance, rapid dry down, and grain quality sufficient to allow storage and shipment to market with minimum loss. The development of these elite inbreds is both labor and capital intensive, requiring many years of evaluation in many different environments. The incorporation of additional traits such as those affecting grain quality would place additional constraints on the plant breeder, dramatically increasing both the time and cost of producing these quality grain inbreds.

Once elite inbreds have been developed, they may be used in several ways to produce commercial hybrid seed. The majority of hybrid seed produced in the United States is of the single cross type. Two inbred lines are intermated to give rise to what is termed an F1 single cross hybrid (A X B). In some instances, the female parent in the cross is itself an F1 hybrid, so that a three-way cross hybrid is produced with the genotype of (A X B) X C. More rarely, a four-way cross hybrid is produced, with both male and female parents as F1 hybrids, resulting in a genotype of (A X B) X (C X D). In all cases, the resulting kernels from this intermating are sold as seed to commercial growers who ultimately harvest F2 grain from the crop for on farm use or commercial sale. A general review of these systems is available in several texts (e.g., Poehlman, J. M., 1987, Breeding Field Crops, 3rd Edition, Avi Publishing Company, Westport, Conn.).

In addition to possessing the proper combination of genetic factors to produce elite hybrids, the inbreds themselves must be reasonably vigorous to support the demands of modern seed production. This can be illustrated by a description of how single cross hybrids are produced commercially. To control the direction of pollination and assure the harvest of predominantly hybrid seed, seed production fields are typically designed so that 4 rows of inbred corn plants serving as females alternate with 1 row of inbred corn plants serving as males, although other planting patterns are possible. The female plants are rendered male sterile either by detasseling, or via genetic mechanisms such as cytoplasmic male sterility which renders the tassel nonfunctional. Ovules borne on these female plants are then fertilized by pollen produced by the male plants, and the resulting hybrid seed borne on the female plants is harvested, cleaned, sized, and treated prior to sale to commercial growers. To produce this hybrid seed economically the male inbred plants need to reliably shed sufficient pollen to fertilize the female plants over a variety of climatic conditions. The hybrid seed borne on the female inbred plants need to be of high quality to allow good germination and early plant vigor in the commercial grower's field, and the female plants themselves need to stand and retain ears until the time of harvest. These requirements of the inbred lines themselves further increase the time and money required to produce commercially successful hybrids.

Thus, the capital- and time-intensive development and testing of inbreds is key to modern corn production. There are three breeding schemes commonly used to produce inbred lines of corn: the pedigree system of breeding, backcross conversion, and recurrent selection. In a commonly practiced form of the pedigree method, two inbred lines of corn, often with different sets of desirable characteristics, are intermated, and superior plants are selected and selfed in succeeding generations to become increasingly inbred. Part of this selection procedure involves a periodic assessment of the performance of the emerging inbred lines in various hybrid combinations. The process of continued selfing and selection, typically over five to eight generations, results in the production of lines which are, to a significant degree, genetically homogeneous or inbred. Development and commercial production of an elite inbred by this method typically takes from 5 to 7 years.

In the second method of breeding, backcross conversion, a desired characteristic (generally, one which is simply inherited, such as certain disease resistances) is introduced into a target elite inbred (the recurrent parent) by intermating the recurrent parent with a source plant expressing a particular trait of interest. This source plant may also be an inbred, but in the broadest sense can be a member of any plant variety or population cross-fertile with the recurrent parent. The progeny of this cross which express the desired characteristic are then (back)crossed to the recurrent parent, desirable progeny identified, and the cycle is repeated. After five to eight cycles of backcrossing and selection, this procedure results in the recovery of the desired characteristic in what is substantially the genetic background of the recurrent, elite parent. Oftentimes the "converted" inbred can be recovered and produced quickly (three to five years), but since the end product is essentially an "older" line in many respects, backcross conversion is generally considered to be a conservative method of inbred development.

The third method of inbred development, recurrent selection, generally involves the extraction of a new inbred from a broad, genetically heterogeneous breeding pool, commonly termed a population. Individual plants within the population are selected for traits of interest such as stalk strength or combining ability and intermated to create a new population from which to again select and intermate individuals with these desired characteristics. Because the number of possible genetic combinations within these populations is quite large, substantial opportunity exists for recovering subpopulations and eventually inbreds with novel grain, seed, or whole plant characteristics. However, an inevitable consequence of this genetic diversity is that it takes substantially longer to develop elite inbreds by recurrent selection than by the preceding two methods.

In summary, all three of the currently available strategies are labor and capital intensive, each requiring many years of effort to allow for both recombination of genetic information and selection to eventually produce elite inbred lines. The rapidity with which satisfactory inbred lines can be developed is determined to a large degree by the nature and number of traits that the lines must possess as dictated by the plant breeder. The addition of novel or unusual traits, especially if controlled by many genes as in the case of oil content, would significantly increase the time and effort required to produce the desired lines.

Most corn grain is handled as a commodity, since many of the industrial and animal feed requirements for corn can be met by common varieties of field corn which are widely grown and produced in volume. However, there exists at present a growing market for corn with special end-use properties which are not met by corn grain of standard composition. Most commonly, specialty corn is differentiated from "normal" field corn by altered endosperm properties, such as an overall change in the degree of starch branching (waxy corn, amylose extender; Glover, D. V. and E. T. Mertz, 1987, Corn, In: Nutritional Quality of Cereal Grains: Genetic and Agronomic Improvement, R. A. Olson and K. J. Frey, eds., American Society of Agronomy, Madison, Wis., pp. 183–336), increased accumulation of sugars or water-soluble polysaccharides (sugary, shrunken, supersweet corn; Glover, D. V. and E. T. Mertz, 1987, Corn, In: Nutritional Quality of Cereal Grains: Genetic and Agronomic Improvement, R. A. Olson and K. J. Frey, eds., American Society of Agronomy, Madison, Wis., pp. 183–336) or alterations in the degree of endosperm hardness (food grade corn, popcorn; Glover, D. V. and E. T. Mertz, 1987, Corn. In: Nutritional Quality of Cereal Grains; Genetic and Agronomic Improvement, R. A. Olson and K. J. Frey, eds. American Society of Agronomy, Madison, Wis., pp. 183–336; Rooney, L. W. and S. O. Serna-Saldivar, 1987, Food Uses of Whole Corn and Dry-Milled Fractions, In: Corn:Chemistry and Technology, S. A. Watson and P. E. Ramstead, eds. American Association of Cereal Chemists, Inc., St. Paul, Minn., pp. 399–429). "Specialty" corn types are typically grown under contract for production for specific end users who place value on starch quality or other specific kernel quality attributes. Perhaps the outstanding example of this differentiation is the contract production of waxy maize, whereby inclusion of a single homozygous recessive gene (wx) converts normal maize starch (75–80% amylopectin, 20–25% amylose) nearly completely to amylopectin (>99%). In a similar fashion the recessive gene amylose extender (ae), when homozygous, increases the specific amylose content of the corn grain to 50% or greater. Additionally, U.S. Pat. No. 4,798,735 teaches how modified corn starches produced by combinations of simple recessive genes can result in the production of starch with useful industrial properties for use in the foods industry. Sweet corn is yet another example of a specialty corn product often grown under contract, where the inclusion of the recessive genes sugary, shrunken-2 or sugary enhancer, singly or in combination, confers sweetness through a reduction in the amount of starch and an increase in the amount of glucose, sucrose, and/or water soluble polysaccharides normally found in the immature corn kernel (Creech, R. and D. E. Alexander, 1978, Breeding for Industrial and Nutritional Quality in Maize, In: Maize Breeding and Genetics, D. B. Walden, ed. John Wiley and Sons, New York, pp. 249–264).

More recently, there is a trend to differentiate corn not only on the basis of alterations in carbohydrate quality but also on the basis of its protein and oil content. Several companies market corn with increased lysine (Crow's Hybrid Corn Company, Milford, Ill.), protein (Wilson Hybrids, Harlan, Iowa) and oil (Pfister Hybrid Corn Company, El Paso, Ill. under the trademark KERNOIL®) levels in an effort to serve markets placing increasing value on these grain components. Protein and oil content are particularly important determinants of the performance of corn as a component of animal feed (Glover, D. V. and E. T. Mertz, 1987, Corn, In: Nutritional Quality of Cereal Grains: Genetic and Agronomic Improvement, R. A. Olson and K. J. Frey, eds. American Society of Agronomy, Madison, Wis., pp. 183–336; Han, Y., C. M. Parsons, and D. E. Alexander, 1987, Nutritive Value of High Oil Corn for Poultry. Poultry Science 66:103–111). Furthermore, as coproducts of wet and dry milling, corn oil and protein are important sources of revenue to wet and dry millers. Recent Iowa State University corn performance trials provide a means for recognizing the industrial value of these corn constitutients by reporting not only the yield of tested hybrids but also their calculated wet milling and feed values. (Iowa Corn Growers Association, 1989, Higher Processing Value in 1989 State Fair Open Class Corn and Soybeans. Bulletin, Aug. 27, 1989)

Pertinent to this application, combinations of recurrent selection and pedigree breeding methods have been used to develop populations and inbreds producing kernels with substantially elevated levels of oil. Perhaps the most thoroughly studied high-oil corn populations are the Illinois High Oil (IHO) and Alexander High Oil (Alexho) populations developed at the University of Illinois. IHO was developed by modified mass selection within the open pollinated corn variety, Burr's White, over more than 80 cycles of selection commencing in 1896 (Alexander, D. E., 1988, High Oil Corn: Breeding and Nutritional Properties, In: Proceedings of the 43rd Annual Corn and Sorghum Industrial Research Conference, pp. 97–105; Dudley, J. W., R. J. Lambert, and D. E. Alexander, 1974, Seventy Generations of Selection for Oil and Protein Concentration in the Maize Kernel, In: Seventy Generations of Selection for Oil and Protein in Maize, J. W. Dudley, ed. Crop Science Society of America, Madison, Wis., pp. 181–212). The highest kernel or grain oil content achieved in this population is about 22% oil on a dry weight basis. In contrast, Dr. Denton Alexander, employing both mass and single kernel selection within a synthetic population (Alexho), was able to achieve an oil content of 22% following only 28 cycles of selection (Alexander, D. E., 1988, High Oil Corn: Breeding and Nutritional Properties, In: Proceedings of the 43rd Annual Corn and Sorghum Industrial Research Conference, pp. 97–105). A number of corn inbreds have been released from the IHO (R802A) and Alexho (R805, R806) populations and are available to the public through the Director of Agricultural Experiment Station, University of Illinois, Urbana, Ill.

Oil content in corn is a grain quality attribute that is quantitatively inherited (Silvela, L., R. Rodgers, A. Garrera and D. E. Alexander, 1989, Effect of Selection Intensity and Population Size on Percent Oil in Maize, Zea mays L. Theoretical and Applied Genetics 78:298–304). Several studies indicate that oil content of bulked F2 kernels arising from crosses between various Alexho derivatives and inbred lines of normal oil content approaches the midparent value of oil content of kernels arising from the self-pollination of each parent separately (Alexander, D. E., 1988, High Oil Corn: Breeding and Nutritional Properties, In: Proceedings of the 43rd Annual Corn and Sorghum Industrial Research Conference, pp. 97–105; Misevic, D., A. Marie, D. E. Alexander, J. Dumanovic, and S. Ratkovic, 1989, Population Cross Diallele Among High Oil Populations of Maize. Crop Sci., 29:613–617). Additionally, F2 grain arising from high-oil X low-oil crosses has been observed to segregate for oil content (Alexander, D. E., 1988, High Oil Corn: Breeding and Nutritional Properties, In: Proceedings of the 43rd Annual Corn and Sorghum Industrial Research Conference, pp. 97–105). Both of these characteristics are consistent with the hypothesis that oil content in corn seed or grain is controlled by the action of several genes, each of which makes a partial contribution to the overall oil content.

Because the genetic heterogeneity is kept high during the initial phases of most recurrent selection programs, it takes substantially longer to develop an agronomically elite inbred from a recurrent selection program than from a program based on pedigree breeding. To date, the majority of high-oil corn exists as populations exhibiting varying degrees of genetic nonuniformity. The widespread production of high-oil corn to meet the needs of poultry producers, swine feeders, and the corn milling industry is substantially delayed now because of limitations of current breeding procedures. Widespread production would be greatly enhanced if new methods of inbred development were found or if new hybrid production practices were available.

SUMMARY OF THE INVENTION

The present invention teaches a novel method for the production of high-oil corn grain by commercial growers. The method results in the production of high-oil corn grain following the pollination of a high-yielding plant by plants containing genes for high oil. The high-oil plants employed as pollinators need not be genetically homozygous (inbred) or even homogeneous in appearance and need not be selected for combining ability with high-yielding female plants. In this way the breeding timeline for the production of commercially successful high-oil parents is significantly and dramatically reduced, and the commercial production of high-oil corn grain is greatly accelerated. This method will catalyze a great expansion in the number of available agronomically elite female plants that can be used for the production of high-oil corn grain, thus increasing the yield and production range of high-oil corn varieties.

Specifically, Applicants have developed a method of enhancing the oil concentration of corn grain comprising the steps of:

(a) planting in close proximity:
  (1) corn seed of a high-yielding variety to obtain female corn plants; and
  (2) corn seed of a high-oil variety which is nonisogenic to said female corn plants to produce high-oil corn plants capable of serving as pollinators;
(b) permitting said high-oil corn plants to pollinate said female corn plants;
(c) harvesting the resulting corn grain on said corn plants, thereby obtaining a high yield of corn grain possessing an oil concentration intermediate between that found in kernels obtained following self-pollination of said high oil and said female corn plants.

DETAILED DESCRIPTION OF THE INVENTION

For purposes of this application, we define the following terms:

Corn. Any variety, cultivar or population of *Zea mays* L.

Elite. This term characterizes a plant or variety possessing favorable traits, such as, but not limited to, high yield, good grain quality, and disease resistance. This enables its use in commercial production of seed or grain at a profit. The term also characterizes parents giving rise to such plants or varieties.

Field corn. These are varieties or cultivars of corn grown extensively in large acreage for the production of grain and/or forage. Most field corn in the United States is also referred to as "dent" corn, whereas field corn produced in Europe and Argentina is more likely to be referred to as "flint" corn.

General Combining Ability. This is the average or overall performance of a genetic strain in a series of crosses.

Germ. This is the embryo of the corn kernel and contains the vast majority of the oil found in the kernel.

Grain. This comprises mature corn kernels produced by commercial growers for on farm use or for sale to customers in both cases for purposes other than growing or reproducing the species. Typical customers would include livestock feeders, wet or dry millers, or animal feed formulators.

Heterozygous. A genetic condition existing when different alleles reside at corresponding loci on homologous chromosomes.

High-Oil Corn (Kernel). A kernel which contains elevated levels of oil on a percent dry weight basis when compared to low-oil corn kernels.

High-Oil Corn (Plant). This is a plant which, when self pollinated, will give rise to kernels containing elevated levels of oil on a percent dry weight basis when compared to a low-oil corn plant.

Homozygous. A genetic condition existing when identical alleles reside at corresponding loci on homologous chromosomes.

Hybrid. Any offspring of a cross between two genetically unlike individuals (Rieger R., A. Michaelis and M. M. Green, 1968, A Glossary of Genetics and Cytogenetics, Springer-Verlag, New York)

Inbred. A substantially homozygous individual or variety.

Kernel. This is the corn caryopsis, consisting of a mature embryo and endosperm which are products of double fertilization. Also, the corn fruit.

Low-Oil Corn (Kernel). A kernels which contains oil in the range of about 2.5–5.1 percent on a dry weight basis.

Low-Oil Corn (Plant). This is a plant which, when self pollinated, will give rise to kernels containing levels of oil in the range of about 2.5–5.1 percent on a dry weight basis. This level of oil is typical of a wide range of field corn inbreds and hybrids.

Maize. This is any variety, cultivar, or population of *Zea mays* L.

Male Sterile. A plant(s) which fails to produce functional pollen as a consequence of mechanical or hand detasseling, incorporation of genetic sterility, or by other mechanisms.

Nonisogenic. A state of genetic dissimilarity between individuals, inbreds, hybrids, or varieties obtained when their nuclear genetic compliments possess less than statistical similarity. Nonisogenicity can be reduced, for example, by backcrossing a variety at least 3 times to a recurrent parent which is itself genetically homogeneous or inbred.

Ovule. This is a structure consisting of female reproductive tissue surrounded by maternal tissue. During the development of a corn plant the ovule will eventually house a haploid egg nucleus and two haploid polar nuclei. Following fusion with sperm nuclei found in pollen, the ovule will develop into a mature corn kernel.

Percent (%) Oil. This is the oil concentration of a corn kernel expressed on a dry weight basis.

Pollen. In corn, this is a structure which ultimately contains the two haploid sperm nuclei which fuse with the egg nucleus and polar nuclei found in the ovule to give rise to the embryo and endosperm of the mature corn kernel.

Population. This is a genetically heterogeneous collection of plants sharing a common genetic derivation.

Seed. This is the mature corn kernel produced for the purpose of propagating the species and for sale to commercial growers.

Specific Combining Ability. This is the performance of specific combinations of genetic strains in crosses in relation to the average performance of all combinations.

Synthetic (Population). This is a genetically heterogeneous collection of plants of known ancestry created by the intermating of any combination of inbreds, hybrids, varieties, populations, races, or other synthetics.

Variety or cultivar. This is a group of similar plants that by structural features and performance can be identified from other varieties within the same species.

The corn kernel is a product of double fertilization (Kiesselbach, T. A., 1980, The Structure and Reproduction of Corn, University of Nebraska Press). This means that both the diploid embryo (giving rise to the germ and seedling) and the triploid endosperm (the nutritive structure surrounding the germ) contain genes transmitted from both the male and female parents. Nonetheless, the genes affecting grain composition and quality are similar enough in most field corn inbreds that crossing any given female with a large variety of male plants does not result in dramatic changes in the compositional or quality characteristics of the resulting seed or grain. Likewise, planting different field corn hybrids within pollinating proximity to each other will not, in most cases, substantially affect the quality of the grain harvested on each type.

In contrast, a minority of commercial corn inbreds or hybrids do contain genes which substantially modify grain quality. These hybrids, such as those containing the waxy gene, must be isolated from normal, non-waxy corn inbreds or hybrids in order to recover waxy seed or grain. If a non-waxy pollen grain (as found in most field corn inbreds and hybrids) pollinates an ovule borne on a waxy inbred or hybrid, the resulting kernel will be non-waxy, even though adjacent kernels on the same ear, pollinated by waxy pollen, will remain waxy. This immediate effect of pollen genotype on kernel characteristics is termed "xenia", (Rieger, R., A. Michaelis and M. M. Green, 1968, A Glossary of Genetics and Cytogenetics, Springer-Verlag, New York) and the hybrid nature of such kernels is recognizable by particular phenotypic characteristics (color, shape, size, etc.) owing to the direct influence exerted by the genotype of the pollen.

This immediate effect of pollen genotype on grain quality has been observed with pollen obtained from high-oil corn plants (Alexander, D. E. and R. J. Lambert, 1968, Relationship of Kernel Oil Content to Yield in Maize Crop Science 8:272–274). We have expanded this observation to develop it into a useful method for producing high-oil corn grain.

The present invention is further defined in the following EXAMPLES, in which all parts and percentages are by dry weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions.

EXAMPLE 1

Demonstration that Kernels Arising on Low-Oil Corn Inbreds Pollinated by High-Oil Male Corn Plants are Themselves High in Oil Low-oil inbreds and high-oil pollinators were grown at the Stine-Haskell Research Center in Newark, Delaware, during the summer of 1989. Low-oil plants used as female were either homozygous for the recessive genes waxy (wx), opaque-2 (o2), or carried the normal alleles at these loci (no designation). Silks arising on ears from these plants were dusted by hand with fresh pollen from high-oil plants which were either high-oil corn inbreds (AEC27-2 S6), partially inbred high-oil corn lines (UHOC3-41 S3; UHOC3-131 S3; UHOC3-168 S3), individuals from a high-oil synthetic population (ASKC28), or individuals from a high-oil corn variety (IHO). Pollination involved bagging immature ears to prevent contamination by stray pollen and collection of fresh pollen in tassel bags as is well known in the breeder's art. Hybrid kernels arising on these ears were harvested by ear at maturity and dried. Bulk kernels on each ear were subjected to intact kernel oil quantity analysis by near infrared transmission spectrophotometry. (Williams, P. C., 1987, Commercial Near Infrared Reflectance Instrumentation, In: Near Infrared Technology in the Agricultural and Food Industries; Williams, P. C. and C. Norris, eds. American Association of Cereal Chemists) Oil values were corrected for moisture and are expressed on a kernel dry weight percentage basis. Midparent values were calculated as the average of the oil values found in self-pollinated grain arising on sib male and sib female plants.

TABLE 1

| FEMALE | | POLLINATOR | | HYBRID KERNELS | | |
|---|---|---|---|---|---|---|
| Source | Percent Oil | Source | Percent Oil | Percent Oil | Mid-parent | Percent Midparent |
| Mo17 | 3.19 | AEC27-2 S6 | 7 | 3.9 | 5.1 | 76 |
| | | UHOC3-131 S3 | 10.5 | 5.6 | 6.9 | 81 |

TABLE 1-continued

| FEMALE | | POLLINATOR | | HYBRID KERNELS | | |
| --- | --- | --- | --- | --- | --- | --- |
| Source | Percent Oil | Source | Percent Oil | Percent Oil | Mid-parent | Percent Midparent |
| | | UHOC3-168 S3 | 12.8 | 5 | 8 | 63 |
| | | ASKC28 | 20.6 | 6.7 | 11.9 | 56 |
| | | IHO | 15.8 | 5.3 | 9.5 | 56 |
| LH51 | 3.34 | UHOC3-168 S3 | 12.8 | 5.7 | 8.1 | 70 |
| | | ASKC28 | 20.6 | 7.3 | 12 | 61 |
| B73 | 3.9 | AEC27-2 S6 | 7 | 4.8 | 5.6 | 86 |
| | | UHOC3-41 S3 | 11.9 | 6.1 | 8.1 | 75 |
| | | UHOC3-168 S3 | 12.8 | 5.9 | 8.5 | 69 |
| | | ASKC28 | 20.6 | 10 | 12.4 | 81 |
| | | IHO | 15.8 | 4.5 | 10 | 45 |
| Mo17 wx | 3.87 | AEC27-2 S6 | 7 | 4.3 | 5.4 | 80 |
| | | UHOC3-41 S3 | 11.9 | 5.8 | 7.9 | 73 |
| | | ASKC28 | 20.6 | 8.4 | 12.2 | 69 |
| LH51 wx | 3.78 | AEC27-2 S6 | 7 | 4.6 | 5.4 | 85 |
| | | UHOC3-41 S3 | 11.9 | 6.4 | 7.9 | 81 |
| | | ASKC28 | 20.6 | 8.7 | 12.2 | 71 |
| | | IHO | 15.8 | 6.3 | 9.8 | 64 |
| B73 HT wx | 3.9* | AEC27-2 S6 | 7 | 5.2 | 5.5 | 95 |
| | | UHOC3-41 S3 | 11.9 | 6.3 | 8 | 79 |
| | | ASKC28 | 20.6 | 10.8 | 12.2 | 89 |
| | | IHO | 15.8 | 5.6 | 9.9 | 57 |
| B37 wx | 3.2 | AEC27-2 S6 | 7 | 5.1 | 5.1 | 100 |
| | | UHOC3-131 S3 | 10.5 | 5.4 | 6.8 | 79 |
| | | UHOC3-168 S3 | 12.8 | 6.9 | 8 | 86 |
| | | ASKC28 | 20.6 | 7.2 | 11.9 | 61 |
| | | IHO | 15.8 | 6.2 | 9.5 | 65 |
| Oh43 wx | 2.6 | AEC27-2 S6 | 7 | 4.B | 4.8 | 100 |
| | | UHOC3-131 S3 | 10.5 | 5.4 | 6.5 | 83 |
| | | UHOC3-168 S3 | 12.8 | 5.8 | 7.7 | 75 |
| | | ASKC28 | 20.6 | 8.9 | 11.6 | 77 |
| | | IHO | 15.8 | 5.7 | 9.2 | 62 |
| A632 wx | 3.9 | AEC27-2 S6 | 7 | 5.1 | 5.4 | 94 |
| | | UHOC3-131 S3 | 10.5 | 5.8 | 7.2 | 81 |
| | | ASKC28 | 20.6 | 8.9 | 12.2 | 73 |
| | | IHO | 15.8 | 8.2 | 9 | 83 |
| LH74 wx | 4.1 | UHOC3-41 S3 | 11.9 | 7 | 8 | 88 |
| | | ASKC28 | 20.6 | 9.8 | 12.3 | 80 |
| | | IHO | 15.8 | 5.7 | 10 | 57 |
| LH82 wx | 4.14 | AEC27-2 S6 | 7 | 6 | 5.6 | 107 |
| | | UHOC3-41 S3 | 11.9 | 6.9 | 8.1 | 85 |
| | | ASKC28 | 20.6 | 11.5 | 12.4 | 93 |
| | | IHO | 15.8 | 4.B | 10 | 48 |
| Mo17 o2 | 3.5* | AEC27-2 S6 | 7 | *4.9 | 5.2 | 94 |
| | | UHOC3-41 S3 | 11.9 | 6.2 | 7.7 | 81 |
| | | UHOC3-168 S3 | 12.8 | 5.7 | 8.1 | 70 |
| | | ASKC28 | 20.6 | 8.7 | 12 | 73 |
| | | IHO | 15.8 | 5.4 | 9.7 | 56 |

*Oil Content of Parent Seed to Female

As shown in Table 1, kernels arising from crosses between a number of low-oil inbred corn lines and high-oil corn plants always contain levels of oil which are significantly higher than seen in the low-oil inbreds themselves. As demonstrated in Table 1, Mo17, LH51, B73, LH51 wx, B73 HT wx, LH74 wx, and LH82 wx Female Source parent corn varieties are available from Holden Foundastion Seed Company, Williamsburg, Iowa. Those denominated Mo17 wx, B73 wx, Oh43 wx, A632 wx, and Mo17 o2 are available from the Maize Genetics Coop, University of Illinois Agronomy Department, University of Illinois, Urbana, Ill. In most cases the oil concentration in the hybrid kernels increases as the concentration of oil in the high-oil corn variety serving as a pollinator increases, although in this trial the amount of oil found in these kernels is generally less than the midparent value. This is true whether the high-oil corn variety serving as pollinator is an inbred, a partially inbred line, members of a synthetic population, or comprise a high-oil variety.

Hybrid kernels arising from pollinations involving IHO appear to be anomolously low in oil content as evidenced by their low percent midparent values. This may be due to the fact that IHO is genealogically distinct from the other high-oil pollinators, and hence may contain genes which behave differently from the other high-oil pollinators employed in this Example.

EXAMPLE 2

Demonstration that Kernels Arising on Low-Oil Corn Hybrids Pollinated by High-Oil Corn Inbreds, and Kernels Arising on High-Oil Corn Hybrids Pollinated by either Low-Oil or High-Oil Corn Inbreds, are Themselves High in Oil Low-oil or high-oil inbreds and hybrids were grown at El Paso, Ill. during the Summer of 1989. Several low-oil [P3377, P3379, Pfister 2995 (Pfister Hybrid Corn Company, El Paso, Ill.)] and high-oil [X124, KERNOIL®-4, X122, X326, and X327all Pfister Hybrid Corn Company, El Paso, Ill.] corn hybrids were used as female and were pollinated by hand with pollen arising on either a low-oil (LH123, Holden Foundation Seed Company, Williamsburg, Iowa) or a high-oil (LP11) inbred. Hand pollinations were accomplished following procedures well known to the breeder's art. Hybrid kernels arising on these ears were harvested by ear at maturity and dried. Bulk kernels from each ear which were subjected to oil analysis were dried to less than 8% moisture. The oil content of intact kernels was determined by wide-line nuclear magnetic resonance spectroscopy (Alexander, D. E., L. Silvela, F. I. Collins, and R. C. Rodgers, 1967, Analysis of Oil Content of Maize by Wide Line NMR, J. Am. Oil Chem. Soc., 44:555–558), and oil concentration expressed on a dry weight percent basis.

TABLE 2

| FEMALE | | POLLINATOR | | HYBRID KERNELS | | |
|---|---|---|---|---|---|---|
| Source | Percent Oil | Source | Percent Oil | Percent Oil | Mid-parent | Percent Midparent |
| P3379 | 4.8 | LP11 | 9.0 | 7.0 | 6.9 | 101 |
| | | LH123 | 4.4 | 4.7 | 4.6 | 102 |
| Pfister 2995 | 4.9 | LP11 | 9.0 | 7.0 | 6.9 | 101 |
| | | LH123 | 4.4 | 4.7 | 4.6 | 101 |
| P3377 | 5.1 | LP11 | 9.0 | 7.1 | 7.0 | 100 |
| | | LH123 | 4.4 | 4.9 | 4.7 | 102 |
| X124 | 6.5 | LP11 | 9.0 | 8.1 | 7.7 | 104 |
| | | LH123 | 4.4 | 5.4 | 5.4 | 100 |
| KERNOIL ®-4 | 7.5 | LP11 | 9.0 | 8.5 | 8.3 | 103 |
| | | LH123 | 4.4 | 6.1 | 6.0 | 103 |
| KERNOIL ®-8 | 7.5 | LP11 | 9.0 | 8.0 | 8.3 | 97 |
| | | LH123 | 4.4 | 6.2 | 6.0 | 104 |
| X326 | 7.5 | LP11 | 9.0 | 8.4 | 8.2 | 103 |
| | | LH123 | 4.4 | 6.0 | 5.9 | 101 |
| X327 | 7.6 | LP11 | 9.0 | 8.3 | 8.3 | 99 |
| | | LH123 | 4.4 | 6.0 | 6.0 | 99 |

The data in Table 2 demonstrate that the xenia effect for oil content was not confined to crosses using only inbred lines as female. The oil content of hybrid grain arising from crosses among either high-oil or low-oil hybrids (used as female) and high-oil inbred varieties serving as pollinators is itself high in oil. Similarly, grain arising from crosses between a high-oil hybrid female and a low-oil inbred male is also high in oil. In contrast, crosses among low-oil hybrids and low-oil inbreds gave rise to grain low in oil content.

In all of the combinations involving at least one high-oil parent the oil content of the kernels harvested on the female plants approach the midparent value. Thus, if a high-oil hybrid female is employed as a parent in a cross, the resulting hybrid kernels arising following pollination by an inbred plant are also high in oil.

EXAMPLE 3

Demonstration that Kernels Arising on Low-Oil Corn Hybrids Pollinated by Hybrids of Increased Oil Content Approach or Exceed Predicted Oil Midparent Values Kernels from the low-oil hybrid PF3450 and several hybrids [X121, X325, X326, X327, X338, and X354: all Pfister Hybrid Corn Company, El Paso, Ill.] high in oil when grown in the central corn growing regions of the United States were sown in a field near Rosario, Argentina in October 1989 and grown during the ensuing season. Hand pollinations among these varieties were performed by procedures well known to the breeders art. Hybrid kernels arising on these ears were harvested by ear at maturity and dried. Bulk kernels on each ear were subjected to intact kernel oil quantity analysis by near infrared transmission spectrophotometry. Oil values were corrected for moisture and are expressed on a kernel dry weight percentage basis. Midparent values were calculated as the average of the oil values found in self-pollinated grain arising on sib male and sib female plants.

TABLE 3

| FEMALE | | POLLINATOR | | HYBRID KERNELS | | |
|---|---|---|---|---|---|---|
| Source | Percent Oil | Source | Percent Oil | Percent Oil | Midparent | Percent Midparent |
| PF3450 | 2.94 | X325 | 4.61 | 4.45 | 3.78 | 118 |
| | | X338 | 4.73 | 4.21 | 3.84 | 110 |
| | | X326 | 4.74 | 4.65 | 3.84 | 121 |
| | | X327 | 4.75 | 4.4 | 3.84 | 115 |
| | | X354 | 5.46 | 4.08 | 4.2 | 97 |
| | | X121 | 5.62 | 4.13 | 4.28 | 97 |

As shown in Table 3, several of the hybrids known to express high-oil when grown in the United States corn belt did not do so in this test in Argentina (X325, X338, X326, X327), although X354 and X121 did classify as high-oil hybrids in this test. Nonetheless, even in this environment, the oil content of the hybrids employed as pollinators was substantially higher than the oil content of the hybrid variety employed as female. Hybrid kernels recovered from these crosses again exhibited oil contents at or above their midparent values. This demonstrates that a Xenia effect for oil quantity is apparent when a hybrid of low-oil content is pollinated by a variety of hybrids containing levels of oil substantially above that of the hybrid employed as female.

Taken together, Examples 1, 2 and 3 indicate that hybrid kernels arising from cross-fertilization of high-oil and low-oil lines contain higher concentrations of oil than that found in the low-oil parent. This is true regardless of whether the male or female plants are themselves hybrid or inbred, and occurs whether the high-oil pollinators comprise members of synthetic populations, open pollinated varieties, or partial inbreds exhibiting varying degrees of genetic homogeneity. A wide variety of inbreds and hybrids exhibiting a range of oil concentrations can be combined by intermating to produce hybrid kernels which are significantly higher in oil content than those borne on the low-oil parent, and in many cases the oil content of the hybrid kernel approaches or even exceeds expected midpoint values.

Examples 1, 2 and 3 broadly illustrate that the inheritance of oil content in corn is subject to a Xenia effect, whereby the oil quantity potential of the male gamete directly influences the oil quantity of F1 hybrid seed or grain. Since plants from two major populations exhibiting high oil, Illinois High Oil and Alexho Synthetic, can confer a high-oil content to F1 hybrid kernels, it is likely that new populations, subpopulations, varieties, hybrids or inbreds derived solely or in part from these populations will also exhibit Xenia for oil. Several inbreds tracing their ancestry to either Alexho Synthetic or Illinois High Oil have been released to the public, including the inbreds R802A, R805 and R806 available from the Director of the Agricultural Experiment Station, University of Illinois, Urbana, Ill. Since oil in corn is inherited quantitatively, it is likely that most or all other high-oil varieties will exhibit a Xenia effect for oil when so tested.

Application of the Xenia effect in a novel method for the production of high-oil corn grain by farmers and commercial growers will ensure prompt availability of important corn products. Preferred, by virtue of its high yield of grain or its high-oil content, is a method consisting of planting a high-yielding F1 hybrid used as female corn plant which would be pollinated by high-oil corn plants with oil concentrations of 10 percent or more. The female hybrid would arise from crosses between a cytoplasmically male sterile inbred and a second inbred which would not restore fertility to the hybrid. Alternatively, the female plants could be rendered male sterile by other methods, such as detasseling. The high-oil corn plants used as pollinators could be either high-oil inbreds, high-oil hybrids, high-oil varieties, high-oil synthetics or exotics or any other suitable germplasm source containing genes for high-oil content and exhibiting a xenia effect for oil. The high-oil plants serving as pollinators could be interplanted with the hybrid female plants, or could be planted in rows alternating with rows containing only low-oil female hybrids. At harvest high-oil grain would be obtained either by the selective harvest of grain arising on the female plant or, if advantageous, grain arising by self-pollination of the high-oil plants serving as pollinators may also be harvested and blended with grain arising on the female plants. Most preferred would be the use of a high-yielding F1 hybrid as the female corn plant, ASK C28 as the nonisogenic variety serving as pollinator with random interplanting of the two types of plants followed by harvesting of the corn grain from all plants.

The instant invention differs significantly from current grain production methods in several important respects. Current grain production methods require that the inbred, hybrid, variety, population, or any other source of germplasm used as the source for high oil would combine well with (i.e., be nonisogenic to) a low-oil parent to produce hybrid seed which would subsequently give rise to an agronomically elite hybrid plant. This high-oil hybrid would then be planted in a grower's field and allowed to open pollinate to produce grain. Long, costly breeding programs are required to provide inbreds which combine well preserving all beneficial traits under current practices. Under the claimed method the primary requirement of the high-oil parent serving as a pollinator would be that it sheds sufficient pollen to efficiently pollinate the high-yielding female plants. This novel method most importantly greatly reduces the breeding timeline and extensive effort necessary to develop high-oil inbred pollinators required for commercial high-oil grain production. This is because the favorable agronomic properties key to successful grain production would already be embodied in the high-yielding hybrid employed as the female plants.

Because the instant invention eliminates many of the constraints placed on the performance of the parental lines necessary to support current grain production methods, it will allow a greatly accelerated introduction of corn grain with economically significant levels of oil into the market place. Current agronomic practices can be utilized allowing the immediate production of high-oil grain by commercial farmers.

Applicants' invention also differs significantly from current grain production methods in that the invention requires that the direction of pollination be specified. In contrast, in current grain production, open and random pollination occurs.

Finally, in the case where the high-oil corn variety serving as the pollinator is genetically uniform (that is, substantially inbred or homozygous) the grain harvested under the claimed method may also be substantially uniform in oil content and overall grain quality. In contrast, F2 grain produced from F1 hybrid seed which is heterozygous for high-oil genes will differ in oil content from seed to seed due to the segregation of oil genes in commercial grain. Since increasing grain oil content is obligatorily associated with increased germ size, grain produced by the conventional method will segregate to some degree for overall kernel quality. Uniform grain quality is an important quality attribute of commercial value to the corn milling industry.

The instant invention or variants of that method will be applicable to the production of any specialty grain which relies on the expression of a kernel quality trait which exhibits a xenia effect. This would be true not only in corn but in any other crop that produces an endosperm including but not limited to sorghum, wheat, rye, triticale, rice, barley, oats, and the various millet genera.

Corn lines X387 has been deposited under terms conforming to the Budapest Treaty in the American Type Culture Collection (ATCC), Rockville, Md. 20852-1776 on Nov. 14, 1990, and bears the ATCC accession number 40917.

Corn line ASK C28 has been deposited under terms conforming to the Budapest Treaty in the American Type Culture Collection (ATCC), Rockville, Md. 20852-1776 on Sep. 30, 1991, and bears the ATCC accession number 75105.

What is claimed is:

1. A method of enhancing the oil concentration of corn grain comprising the steps of:
   (a) planting in close proximity:
      (1) corn seed of a high-yielding variety to obtain female corn plants wherein said female corn plants have been rendered male sterile by genetic, mechanical, chemical or a combination of such methods; and
      (2) corn seed of a high-oil concentration variety which is nonisogenic to said female corn plants to produce high-oil concentration corn plants capable of serving as pollinators;
   (b) permitting said high-oil concentration corn plants to pollinate said female corn plants;
   (c) harvesting the resulting corn grain on said corn plants, thereby obtaining a high yield of corn grain possessing an oil concentration intermediate between that found in kernels obtained following self-pollination of said high-oil concentration corn plants and said female corn plants.

2. The method of claim 1, wherein the female corn plants are agronomically elite F1 hybrids of high yield, but are low in oil concentration.

3. The method of claim 1 wherein the female corn plants are high in oil concentration.

4. The method of claim 1, wherein the high-oil concentration corn plants serving as pollinators are high-oil concentration inbreds.

5. The method of claim 1, wherein the high-oil concentration corn plants serving as pollinators are high-oil concentration hybrids.

6. The method of claim 1, wherein the high-oil concentration corn plants serving as pollinators comprise a population containing high-oil concentration plants.

7. The method of claim 1, wherein the high-oil concentration corn plants serving as pollinators comprise an open pollinated variety of high oil corn.

8. The method of claim 1, wherein the high-oil concentration corn plants serving as pollinators are hybrids derived from a cross of standard field corn lines and a high oil concentration corn plant selected from the group consisting of high-oil concentration inbreds, high oil concentration hybrids, a population containing high-oil concentration plants, and an open pollinated variety of high oil corn.

9. The method of claim 6 wherein said high-oil concentration corn plants are members of the group consisting of Alexho Synthetic, Ultra High Oil, Alexho Elite populations, the Illinois versions of the Disease Oil, Iowa 2-Ear, Reid Yellow Dent, and Iowa Stiff Stalk Synthetic populations which have also been selected for high oil concentration.

10. The method of claim 6, wherein male corn plants arise from the Illinois High Oil version of the variety Burr's White.

11. The method of claim 1 wherein said corn plants are grown in an alternating pattern of rows containing female corn plants or high-oil concentration corn plants capable of serving as pollinators, and only grain arising on said female corn plants is harvested.

12. The method of claim 1 wherein said female corn plants and said high-oil concentration corn plants capable of serving as pollinators are interplanted randomly within a row, and grain from both said female corn plants and said high-oil concentration corn plants capable of serving as pollinators is harvested.

13. The method of claim 12 wherein said female corn plants are derived from seed of a high-yielding F1 hybrid and said high-oil concentration corn plants capable of serving as pollinators are derived from seed of ASK C28.

14. A method of claim 1 wherein said corn seed of a high-yielding variety arises from a cross between a cytoplasmically male sterile inbred and a second inbred which does not restore fertility to said high-yielding variety to obtain female corn plants.

* * * * *